United States Patent
Reuter et al.

(10) Patent No.: US 10,716,310 B2
(45) Date of Patent: *Jul. 21, 2020

(54) STRAINS OF BACILLUS FOR INHIBITING FOODBORNE PATHOGENS

(71) Applicant: Phibro Animal Health Corporation, Teaneck, NJ (US)

(72) Inventors: Christopher J. Reuter, Parrish, FL (US); Steven J. MacKenzie, Sarasota, FL (US); Lauren G. Danielson, Bradenton, FL (US); Vincent Scuilla, Sarasota, FL (US)

(73) Assignee: Phibro Animal Health Corporation, Teaneck, NJ (US)

( * ) Notice: Subject to any disclaimer, the term of this patent is extended or adjusted under 35 U.S.C. 154(b) by 1258 days.

This patent is subject to a terminal disclaimer.

(21) Appl. No.: 14/208,959

(22) Filed: Mar. 13, 2014

(65) Prior Publication Data

US 2015/0257400 A1  Sep. 17, 2015

(51) Int. Cl.
*A23B 4/22* (2006.01)
*A61K 35/742* (2015.01)

(52) U.S. Cl.
CPC .............. *A23B 4/22* (2013.01); *A61K 35/742* (2013.01); *Y02A 50/473* (2018.01); *Y02A 50/481* (2018.01)

(58) Field of Classification Search
None
See application file for complete search history.

(56) References Cited

U.S. PATENT DOCUMENTS

| | | | |
|---|---|---|---|
| 6,291,426 B1 | 9/2001 | Heins et al. | |
| 6,498,137 B1 * | 12/2002 | Schalitz et al. | 510/530 |
| 8,236,549 B2 | 8/2012 | Kang et al. | |
| 8,338,160 B2 | 12/2012 | Tzeng et al. | |
| 8,377,455 B2 | 2/2013 | Ceri et al. | |
| 8,404,476 B2 | 3/2013 | Fernandez Martinez et al. | |
| 2003/0106499 A1 * | 6/2003 | Yamada | A01K 61/008 119/207 |
| 2004/0009160 A1 * | 1/2004 | Villamar | A23K 1/004 424/93.46 |
| 2005/0031732 A1 * | 2/2005 | Suhr-Jessen | A23K 1/009 426/2 |
| 2012/0177620 A1 | 7/2012 | Farmer | |
| 2013/0136695 A1 | 5/2013 | Hargis et al. | |

FOREIGN PATENT DOCUMENTS

WO   WO 03103692 A1 * 12/2003 ............. A23K 1/004

OTHER PUBLICATIONS

Li, K et al. Beneficial effects of Bacillus licheniformis on the intestinal microflora and immunity of the white shrimp, *Litopenaeus vannamei*. Biotechnology Letters. 2007. 29: 525-530.*
Tinh, N et al. A review of the functionality of probiotics in the larviculture food chain. Marine Biotechnology. Jan. 2008. 10(1): 1-12.*
Maketon, M et al. Efficacies of some beneficial bacteria on the colonization and inhibition of Vibrio harveyi in black tiger shrimp (*Penaeus monodon* Fabricus) larvae. Kasetsart J. (Nat. Sci.). 2004. 38: 393-399.*
Vinoj, G et al. Inhibitory effects of Bacillus licheniformis (DAB1) and Pseudomonas aeruginosa (DAP1) against Vibrio parahaemolyticus isolated from Fenneropenaeus indicus. Agracult. Int. 2013. Published online Jan. 3, 2013. 21: 1121-1135.*
Machine translation for CN 103173397, date of publication of application Jun. 26, 2013, 5 pages.
International Search Report dated Jul. 20, 2015, Form PCT/ISA/220 (dated Jul. 2014), 12 pages.
He, L. et al. "Synergetic activity of nisin with cell-free supernatant of *Bacillus licheniformis* ZJU12 against food-borne bacteria," (abstract only), Oct. 2006, 1 page.
Kaewklom, S. et al., "Control of *Listeria monocytogenes* on sliced bologna sausage using a novel bacteriocin, amysin, produced by *Bacillus amyloliquefaciens* isolated from Thai shrimp paste (Kapi)," (abstract only), Aug. 2013, 2 pages.
E. Madhava Charyulu et al., "Antimicrobial activity of secondary metabolite from marine isolate *Pseudomonas* sp. against Gram positive and negative bacteria including MRSA", Indian Journal of Experimental Biology, vol. 47, Dec. 2009, pp. 964-968.

* cited by examiner

*Primary Examiner* — Renee Claytor
*Assistant Examiner* — Susan E. Fernandez
(74) *Attorney, Agent, or Firm* — Klarquist Sparkman, LLP

(57) ABSTRACT

A process for inhibiting foodborne pathogens and reducing foodborne disease involves contacting a living animal, a dressed carcass, or a cut of meat with an effective amount of a *bacillus* strain exhibiting antibacterial activity. Strains of antibacterial *bacillus* that are particularly effective for inhibiting Vibrio were discovered. These include *Bacillus licheniformis* OBT 712 and *Bacillus amyloliquefaciens* OBT 618.

6 Claims, 5 Drawing Sheets

Specification includes a Sequence Listing.

```
                      B licheniformos-HB8-16S-rRNA-seq fasta
>B.licheniformos HB8
TGGAGAGTTTGATCCTGGCTCAGGACGAACGCTGGCGGCGTGCCTAATACATGCAAGTCGAGCGGACCGACGGGAGCTTGCTCC
CTTAGGTCAGCGGCGGACGGGTGAGTAACACGTGGGTAACCTGCCTGTAAGACTGGGATAACTCCGGGAAACCGGGGCTAATAC
CGGATRCTTGATTGAACCGCATGGTTCAATTATAAAAGGTGGCTTTTAGCTACCACTTACAGATGGACCCGCGGCGCATTAGCT
AGTTGGTGAGGTAACGGCTCACCAAGGCAACGATGCGTAGCCGACCTGAGAGGGTGATCGGCCACACTGGGACTGAGACACGGC
CCAGACTCCTACGGGAGGCAGCAGTAGGGAATCTTCCGCAATGGACGAAAGTCTGACGGAGCAACGCCGCGTGAGTGATGAAGG
TTTTCGGATCGTAAAACTCTGTTGTTAGGGAAGAACAAGTACCGTTCGAATAGGGCGGTACCTTGACGGTACCTAACCAGAAAG
CCACGGCTAACTACGTGCCAGCAGCCGCGGTA
```

FIGURE 1

B_amyloliquefaciens-OB5-16S-rRNA-seq fasta
>B.amyloliquefaciens OB5
TGGAGAGTTTGATCCTGGCTCAGGACGAACGCTGGCGGCGTGCCTAATACATGCAAGTCGAGCGGACAGATGGGAG
CTTGCTCCCTGATGTTAGCGGCGGACGGGTGAGTAACACGTGGGTAACCTGCCTGTAAGACTGGGATAACTCCGGG
AAACCGGGGCTAATACCGGATGGTTGTTTGAACCGCATGGTTCAGACATAAAAGGTGGCTTCGGCTACCACTTACA
GATGGACCCGCGGCGCATTAGCTAGTTGGTGAGGTAACGGCTCACCAAGGCrACGATGCGTAGCCGACCTGAGAGG
GTGATCGGCCACACTGGGACTGAGACACGGCCCAGACTCCTACGGGAGGCAGCAGTAGGGAATCTTCCGCAATGGA
CGAAAGTCTGACGGAGCAACGCCGCGTGAGTGATGAAGGTTTTCGGATCGTAAAGCTCTGTTGTTAGGGAAGAACA
AGTGCCGTTCAAATAGGGCGGCACCTTGACGGTACCTAACCAGAAAGCCACGGCTAACTACGTGCCAGCAGCCGCG
GTA

FIGURE 2

SEQUENCE LISTING

```
<160> NUMBER OF SEQ ID NOS: 2

<210> SEQ ID NO 1
<211> LENGTH: 536
<212> TYPE: DNA
<213> ORGANISM: Bacillus licheniformis

<400> SEQUENCE: 1
tggagagttt gatcctggct caggacgaac gctggcggcg tgcctaatac atgcaagtcg      60
agcggaccga cgggagcttg ctcccttagg tcagcggcg acgggtgagt aacacgtggg     120
taacctgcct gtaagactgg gataactccg ggaaaccggg gctaataccg gatrcttgat    180
tgaaccgcat ggttcaatta taaaaggtgg cttttagcta ccacttacag atggacccgc    240
ggcgcattag ctagttggtg aggtaacggc tcaccaaggc aacgatgcgt agccgacctg    300
agagggtgat cggccacact gggactgaga cacggcccag actcctacgg gaggcagcag    360
tagggaatct tccgcaatgg acgaaagtct gacggagcaa cgccgcgtga gtgatgaagg    420
ttttcggatc gtaaaactct gttgttaggg aagaacaagt accgttcgaa tagggcggta    480
ccttgacggt acctaaccag aaagccacgg ctaactacgt gccagcagcc gcggta        536

<210> SEQ ID NO 2
<211> LENGTH: 535
<212> TYPE: DNA
<213> ORGANISM: Bacillus amyloliquefaciens

<400> SEQUENCE: 2
tggagagttt gatcctggct caggacgaac gctggcggcg tgcctaatac atgcaagtcg      60
agcggacaga tgggagcttg ctccctgatg ttagcggcgg acgggtgagt aacacgtggg     120
taacctgcct gtaagactgg gataactccg ggaaaccggg gctaataccg gatggttgtt    180
tgaaccgcat ggttcagaca taaaaggtgg cttcggctac cacttacaga tggacccgcg    240
```

-continued

```
gcgcattagc tagttggtga ggtaacggct caccaaggcr acgatgcgta gccgacctga    300
gagggtgatc ggccacactg ggactgagac acggcccaga ctcctacggg aggcagcagt    360
agggaatctt ccgcaatgga cgaaagtctg acggagcaac gccgcgtgag tgatgaaggt    420
tttcggatcg taaagctctg ttgttaggga agaacaagtg ccgttcaaat agggcggcac    480
cttgacggta cctaaccaga aagccacggc taactacgtg ccagcagccg cggta         535
```

STRAINS OF BACILLUS FOR INHIBITING FOODBORNE PATHOGENS

CROSS-REFERENCE TO RELATED APPLICATIONS

Not Applicable.

FIELD OF THE DISCLOSURE

This disclosure relates to the use of *bacillus* strains to inhibit the growth, reproduction or propagation of foodborne pathogens to improve food safety and reduce incidents of disease such as gastroenteritis.

BACKGROUND OF THE DISCLOSURE

Foodborne disease caused by contamination from pathogenic bacteria is likely responsible for millions of illnesses annually (at least about 8 million in the United States of America annually according to CDC 2011 estimates), thousands of which result in hospitalization annually, and about 1000 fatalities annually. Foodborne disease generally occurs with at least a similar frequency throughout the world and is the leading cause of illness and death in certain parts of the world.

Known antibacterial agents such as alcohols, chlorine, peroxides, aldehydes, triclosan, triclocarban, and benzalkonium chloride are unsuitable for use in foods due to their inherent toxicity. Treatment with gaseous antibacterial agents (such as ozone or ethylene oxide) or irradiation (such as with ionizing radiation or x-rays) can be safe, effective and economically advantageous in certain cases, but are not favorably perceived by the public. Such techniques have also been criticized by public interest groups and public health experts for various reasons, including allegations that these techniques can mask food spoilage, discourage adherence to good food processing practices, kill beneficial bacteria (e.g., probiotics), denature or degrade nutrients, impair flavor and leave bacterial toxins that were present before the treatment.

*Bacillus* strains exhibiting antifungal activity and the use of such bacteria to control plant diseases are described in the literature (e.g., U.S. Pat. No. 6,291,426).

Antibacterial activity of secondary metabolites obtained from *Pseudomonas* strains has been reported in the literature (e.g., E. Madhava Charyulu et al., Indian Journal of Experimental Biology, Vol. 47, December 2009, pp. 964-968). It was proposed that such secondary metabolites could be useful in new drugs such as antimicrobial drugs.

Accordingly, new and effective methods of reducing foodborne disease are desired.

SUMMARY OF THE DISCLOSURE

Disclosed is a method of inhibiting foodborne pathogens and thereby reducing foodborne disease by applying to or feeding to a living animal, an animal carcass or to cuts of meat an effective amount of a *bacillus* strain exhibiting antibacterial activity.

Also disclosed are specific strains of antibacterial bacilli that are particularly effective at inhibiting *Vibrio*. These include *Bacillus licheniformis* OBT 618, characterized by the sequence shown in FIG. 1 and *Bacillus amyloliquefaciens* OBT 712, characterized by the sequence shown in FIG. 2.

BRIEF DESCRIPTION OF THE DRAWINGS

FIG. 1 (SEQ ID NO: 1) is the relevant sequence for *Bacillus licheniformis* OBT 618.

FIG. 2 (SEQ ID NO: 2) is the relevant sequence listing for *Bacillus amyloliquefaciens* OBT 712.

DESCRIPTION OF THE DISCLOSED EMBODIMENTS

It has been discovered that foodborne pathogens can be inhibited when contacted with an effective amount of a *bacillus* strain exhibiting antibacterial activity.

The term "inhibit" means to reduce or arrest growth and/or reproduction of bacterial pathogens that can cause foodborne diseases, and encompasses killing such bacterial pathogens.

The term "effective amount" means an amount that will achieve a desired level of foodborne pathogen inhibition to effect a beneficial result such as reducing bacterial pathogen populations in or on food, or in or on animals that are processed into foods.

Foodborne pathogens that can be inhibited include *Salmonella* enteric, *Escherichia coli*, *Clostridium difficile* and *Vibrio*.

*Bacillus* strains exhibiting antibacterial activity include *Bacillus licheniformis* strains (e.g., OBT 618), and *Bacillus amyloliquefaciens* strains (e.g., OBT 712). The relevant sequence listings for *Bacillus licheniformis* OBT 618 and *Bacillus amyloliquefaciens* OBT 712 are shown in FIGS. 1 and 2, respectively.

The step of contacting the foodborne pathogens with a *bacillus* strain exhibiting antibacterial activity can involve application of an aqueous based composition containing the antibacterial *bacillus* strain to a live animal, a dressed carcass or cuts of meat, such as by spraying, brushing or dipping. In the case of aquatic animals, the antibacterial *bacillus* strain can be added to a container, tank or enclosure (e.g., a fish hatchery) in which the aquatic animals are raised and/or from which they are harvested. As another alternative, contact between the bacterial pathogens and the antibacterial *bacillus* can be achieved by feeding the antibacterial *bacillus* to the animal, either directly or to animals that serve as the food source for the animal that is ultimately processed for consumption such as by a human or companion animal.

Figure 3:
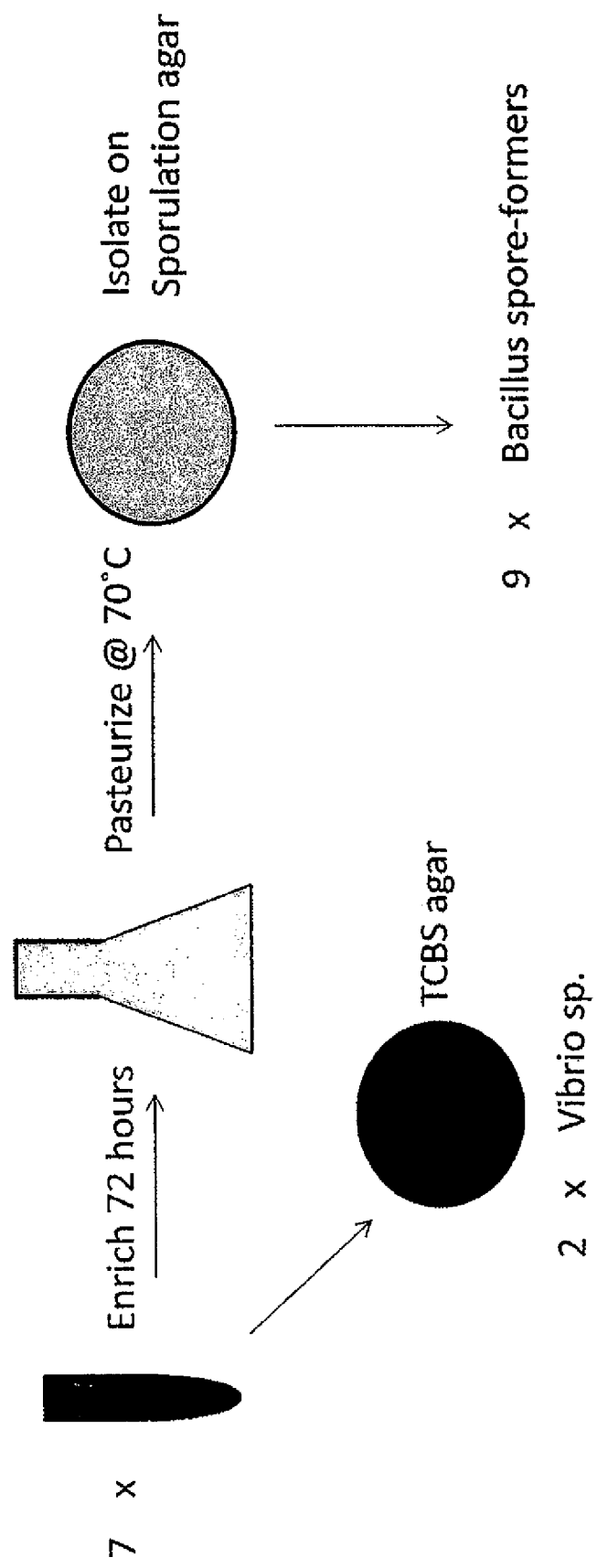
FIG. 3 is a schematic illustration of the preparation of an antibacterial *bacillus* strain isolate.

FIG. 3 shows a method of preparing an antibacterial *bacillus* strain isolate. Samples from marine environments were selected for spore-forming *bacillus* and *Vibrio* species. The *bacillus* samples were enriched, and subsequently pasteurized at about 70° C. *Bacillus* isolates were then placed on sporulation agar. The *Vibrio* was placed on thiosulfate-citrate-bile salts-sucrose (TCBS) agar.

Figure 4:
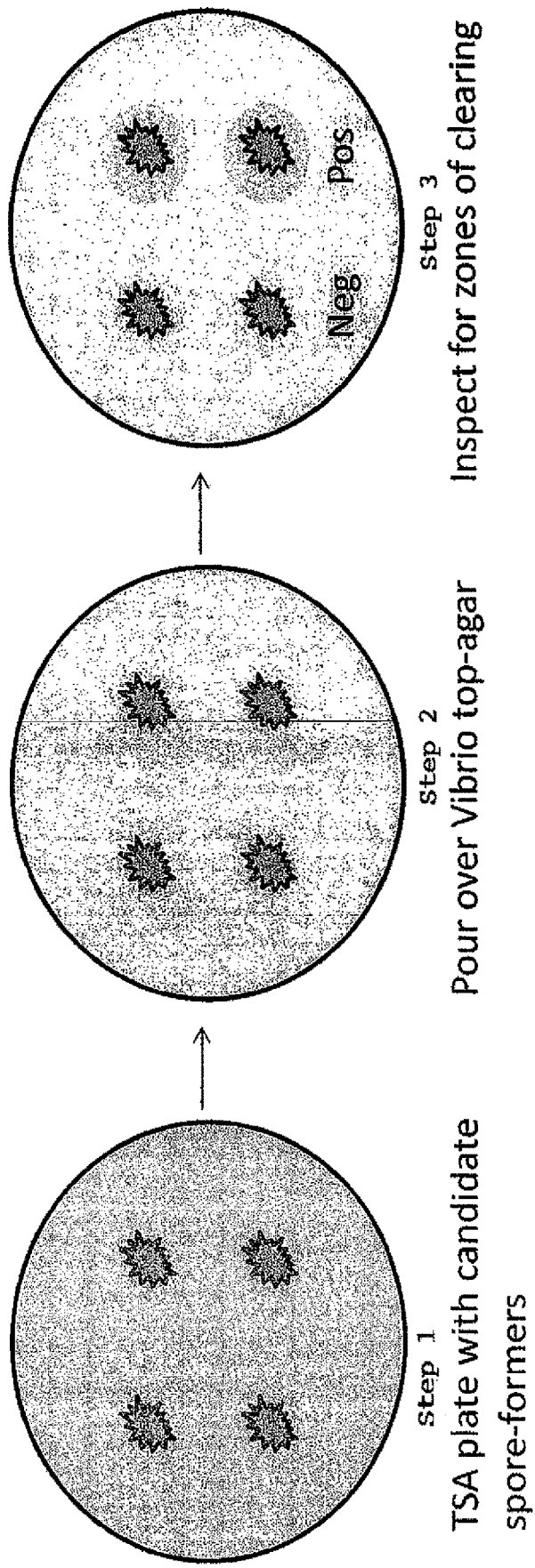
FIG. 4 is a schematic illustration of a process for screening isolates that are antagonistic toward an isolate of *Vibrio* sp. selected from a marine environment using an agar overlay method.

FIG. 4 shows an assay to determine growth inhibition for the *bacillus* strains. A candidate *bacillus* spore-former is placed on a trypticase soy agar (TSA) plate, and thereafter, *Vibrio* isolate embedded in top agar is disposed over the TSA plate. After a sufficient period (e.g., two days), the zones in which the candidate *bacillus* strains are overlaid with the *Vibrio* isolates are inspected for clearance of the *Vibrio*. Positive results are illustrated on the right side of the agar dish at Step 3 of FIG. 4.

Figure 5:
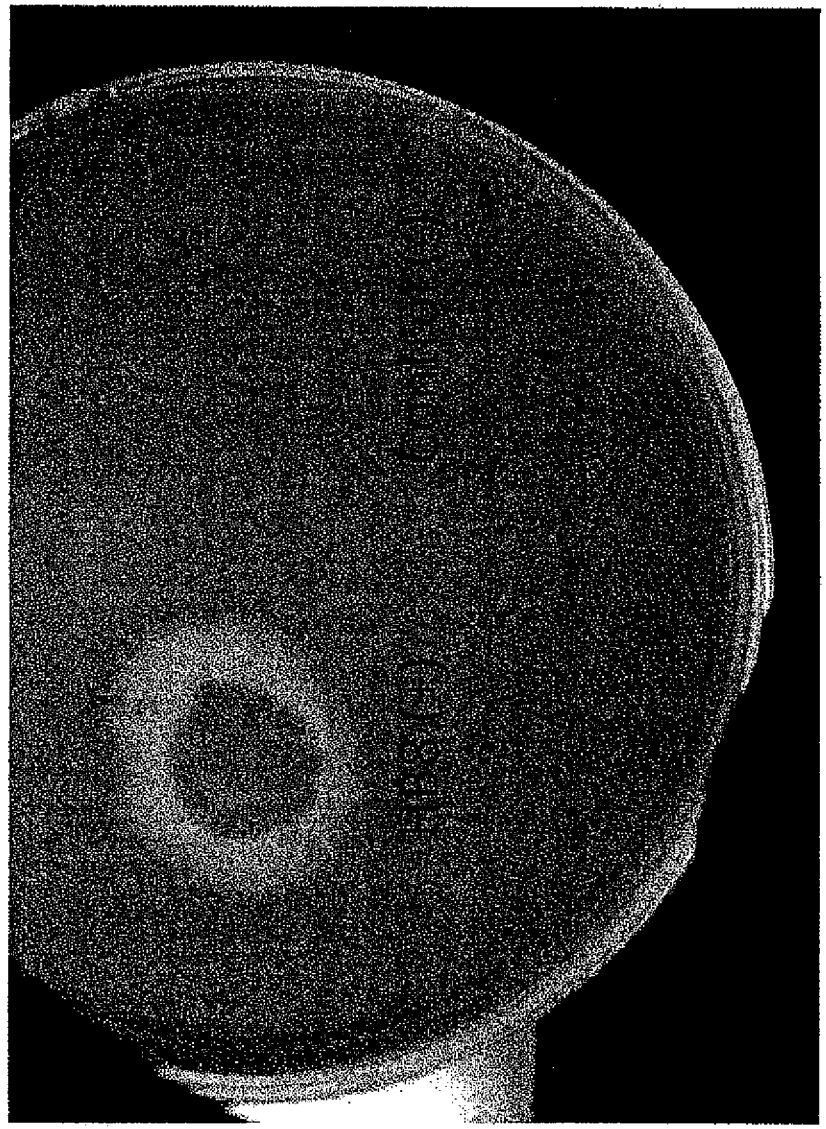
FIG. 5 is a photograph showing a comparison of a positive ("+") result for *Bacillus amyloliquefaciens* OBT 712 to a negative ("−") control.

FIG. 5 is a photograph showing an actual positive result labeled "HB8(+)" and a negative result labeled "Control (−)."

Isolates were screened for antagonism toward an isolate of *Vibrio* sp. selected from a marine environment using an agar overlay method. This method consisted of covering one day old *bacillus* cultures with the *Vibrio* isolate embedded in agar. Zones of clearance were evaluated at 2 days. Thirty-six isolates from various environments were screened. Of the thirty-six isolates tested, two isolates, a *B. licheniformis* (OBT 618) and a *B. amyloliquefaciens* (OBT 712), had particularly high levels of antagonism toward *Vibrio*. All strains are easily propagated on trypticase soy agar (TSA) and sporulate in liquid media.

These strains are antagonistic to *Vibrio*. They produce a clearance zone on agar plates when the *Bacillus* colonies are covered with a thin agar layer that includes *Vibrio* sp. One isolate has a delayed response killing the *Vibrio* after it has grown. The other inhibits *Vibrio* growth.

In a preliminary trial, feeding rotifers the *Bacillus* strains increased survivability of larval snook fed the rotifers. The mechanism by which the *Bacillus* isolates fed to rotifers increases survivability of larval snook fed the rotifers has not been determined. It is conceivable that they are inhibiting growth of *Vibrio* within the digestive tract of rotifers or snook. It is also possible that they inhibit growth of *Vibrio* within larval brooding tanks overall.

Anticipated use is at a concentration of $10^5$-$10^7$ spores/ml in live food tanks or in a larval rearing tank. They are stored as freeze dried spores. Spores can be supplied on a nutritive carrier.

The invention could possibly be used to suppress *Vibrio* sp. on multiple fish species as well as shell fish that are grown in culture. *Vibrio* is a gammaproteobacteria, a class of bacteria that includes *Pseudomonas* and *Enterobacter* such as *E. coli* and *Salmonella* sp. It could potentially be antagonistic to these other species.

Possible ancillary benefits of *Bacillus* addition in aquaculture include improved nutrient availability and waste reduction.

The *Bacillus licheniformis* strain OBT 618 was deposited under the Budapest Treaty and will be irrevocably and without restriction or condition released to the public upon issuance of a patent. The *Bacillus licheniformis* strain OBT 618 was deposited May 29, 2015 at the American Type Culture Collection (ATCC), P.O. Box 1549, Manassas, VA 20108 and given accession number PTA-122188.

The described embodiments are preferred and/or illustrated, but are not limiting. Various modifications are considered within the purview and scope of the appended claims.

What is claimed is:

1. A process for inhibiting foodborne pathogenic bacteria, comprising contacting a living animal, dressed carcass, or cut of meat with an effective amount of *Bacillus licheniformis* strain OBT 618 as deposited with the American Type Culture Collection under accession number PTA-122188 that exhibits antibacterial activity.

2. The process of claim 1, in which a foodborne pathogenic bacteria is known to be present in or on the living animal, dressed carcass, or cut of meat.

3. The process of claim 2, in which the foodborne pathogenic bacteria is *Vibrio*.

4. The process of claim 1, in which contacting the living animal, dressed carcass, or cut of meat with the *Bacillus* strain is done by applying an aqueous based composition containing the *Bacillus* strain to the live animal, dressed carcass, or cut of meat.

5. The process of claim 4, in which the applying is done by spraying, brushing or dipping.

6. The process of claim 1, in which the process is performed on a living animal, and the contacting is done by feeding the antibacterial *Bacillus* to the living animal.

* * * * *